United States Patent [19]

Bundy

[11] 3,983,157

[45] Sept. 28, 1976

[54] 4-OXA PHENYL-SUBSTITUTED PGF COMPOUNDS

[75] Inventor: Gordon L. Bundy, Portage, Mich.

[73] Assignee: The Upjohn Company, Kalamazoo, Mich.

[22] Filed: Oct. 23, 1975

[21] Appl. No.: 625,180

Related U.S. Application Data

[60] Division of Ser. No. 459,759, April 11, 1974, Pat. No. 3,931,289, which is a continuation of Ser. No. 185,448, Sept. 30, 1971, abandoned, which is a continuation-in-part of Ser. No. 103,338, Dec. 31, 1970, abandoned.

[52] U.S. Cl............................ 260/473 A; 260/345.8; 260/520 B
[51] Int. Cl.$^2$.......................................... C07C 69/76
[58] Field of Search.......... 260/473 A, 520 B, 345.8

[56] References Cited

UNITED STATES PATENTS 3,864,387   2/1975   Nelson............................ 260/473 A

FOREIGN PATENTS OR APPLICATIONS 7,118,204   5/1972   Netherlands........................ 260/473

*Primary Examiner*—Paul J. Killos
*Attorney, Agent, or Firm*—Morris L. Nielsen

[57] ABSTRACT

This invention is a group of 3-oxa and 4-oxa phenyl-substituted PGE type, PGF type, PGA type and PGB type compounds, and processes for making those. These compounds are useful for a variety of pharmacological purposes, including anti-ulcer, inhibition of platelet aggregation, increase of nasal patency, labor inducement at term, and wound healing.

32 Claims, No Drawings

4-OXA PHENYL-SUBSTITUTED PGF COMPOUNDS

CROSS REFERENCE TO RELATED APPLICATIONS

This is a division of application Ser. No. 459,759, filed Apr. 11, 1974, now U.S. Pat. No. 3,931,289, which is a continuation of my copending application Ser. No. 185,448, filed Sept. 30, 1971, now abandoned, which was a continuation-in-part of my copending application Ser. No. 103,338 filed Dec. 31, 1970, and now abandoned.

DESCRIPTION OF THE INVENTION

This invention relates to novel compositions of matter, to novel methods for producing them, and to novel chemical intermediates useful in those processes. Particularly, this invention relates to certain novel analogs of prostaglandins $E_1$, $E_2$, $F_{1\alpha}$, $F_{1\beta}$, $F_{2\alpha}$, $F_{2\beta}$, $A_1$, $A_2$, $B_1$, $B_2$, and the dihydro derivatives of the $PG_1$ compounds. These novel analogs each have an oxa oxygen (—O—) in place of the methylene (—$CH_2$—) moiety at the 3-position or at the 4-position of the prostanoic acid structure and also have a benzene ring as part of the C–13 to C–20 chain of the prostanoic acid.

The essential material for this application, including the background of the invention, the disclosure of the invention, and the description of the preferred embodiments, including Preparations and Examples, is incorporated by reference from U.S. Pat. No. 3,931,289, columns 1–101, inclusive, under the provisions of M.P.E.P. 608.01(p).

The following formulas represent the novel 4-oxa phenyl-substituted prostaglandin analogs of this invention:

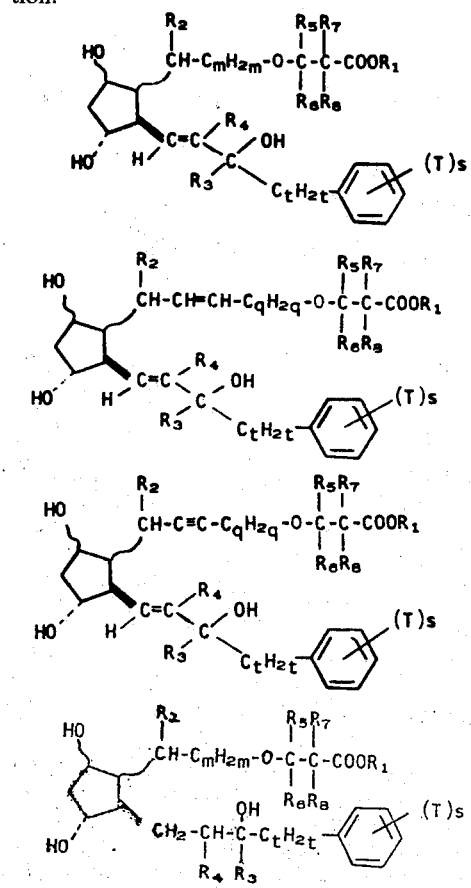

Formulas XX, XXII, XXIV, and XXVI represent 4-oxa phenyl-substituted compounds of the PGE type.

In those formulas, $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or ethyl substituted in the $\beta$-position with 3 chloro, 2 or 3 bromo, or 1, 2, or 3 iodo. $R_2$, $R_3$, $R_4$, $R_5$, $R_6$, $R_7$, and $R_8$ are hydrogen or alkyl of one to 4 carbon atoms, inclusive. The divalent moiety —$C_nH_{2n}$— represents alkylene of one to 10 carbon atoms, inclusive, with one to 5 carbon atoms, inclusive, between —$CHR_2$— and —O—. The divalent moiety —$C_mH_{2m}$ represents alkylene of one to 9 carbon atoms, inclusive, with one to 4 carbon atoms, inclusive, between —$CHR_2$— and —O—. The divalent moiety —$C_pH_{2p}$— represents alkylene of one to 8 carbon atoms inclusive, with one, 2, or 3 carbon atoms between —CH≡CH— or —C≡C— and —O—. The divalent moiety —$C_qH_{2q}$—represents alkylene of one to 7 carbon atoms, inclusive, with 1 or 2 carbon atoms between —CH=CH— or —C≡C— and —O—. The moiety —$C_tH_{2t}$— represents a valence bond, i.e., wherein $t$ is zero, or alkylene of one to 10 carbon atoms, inclusive, i.e., wherein $t$ is one to 10, substituted with zero, one, or 2 fluoro, with one to 7 carbon atoms, inclusive, between —$CR_3OH$— and the ring. When one or 2 fluoro are present as substituents of —$C_tH_{2t}$—, that moiety will contain $2t-1$ or $2t-2$ hydrogen atoms, respectively, rather than $2t$ hydrogen atoms. The symbol T represents alkyl of one to 4 carbon atoms, inclusive, fluoro, chloro, trifluoromethyl, or —$OR_8$, wherein $R_8$ is hydrogen, alkyl of one to 4 carbon atoms inclusive, or tetrahydropyranyl. The symbol $s$ represents zero, one, 2 or 3. Regarding the combination $(T)_s$ attached to the phenyl ring, no more than two T are other than alkyl. Except for that proviso, when two or three T are present as substituents, they are the same or different.

In the case of the compounds of formulas XX, XXI, XXIV, and XXVI, there are two wavy lines, and those formulas encompass compounds wherein the configurations of the hydroxy and the carboxyl-terminated moieties are, respectively, $\alpha,\alpha$, $\alpha,\beta$, $\beta,\alpha$, and $\beta,\beta$.

Formulas XX, XXII, XXIV, and XXVI include lower alkanoates, and also pharmacologically acceptable salts when $R_1$ is hydrogen.

Also included in Formulas XX, XXII, XXIV, and XXVI are separate isomers wherein the side chain hydroxy is in S or R (epi) configuration.

Included in Formula XXII are both the cis and the trans compounds with respect to the carbon-carbon double bond in the carboxy-terminated side chain. In all of the compounds containing —CH=$CR_4$—, that carbon-carbon double bond is in trans configuration, and the chain containing $R_4$ is attached to the cyclopentane ring in beta configuration in compounds encompassed by Formulas XX, XXII, EEIV, and XXVI.

The novel 4-oxa phenyl-substituted prostaglandin analogs of this invention include racemic compounds and both optically active enantiomeric forms thereof. As discussed hereinabove, two structural formulas are required to define accurately these racemic compounds. For convenience, only a single structural formula is used, for example, Formulas XX, XXII, XXIV, and XXVI, to define the racemic form and both enantiomeric forms of each group of novel prostaglandin analogs. Each formula is, however, to be construed as including said racemic forms and both of said optically active enantiomeric forms.

I claim as my invention:
1. A compound of the formula:

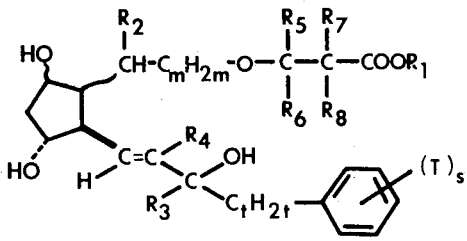

wherein $R_1$ is hydrogen, alkyl of one to 8 carbon atoms, inclusive, cycloalkyl of 3 to 10 carbon atoms, inclusive aralkyl of 7 to 12 carbon atoms, inclusive, phenyl, phenyl substituted with one, 2, or 3 chloro or alkyl of one to 4 carbon atoms, inclusive, or ethyl substituted in the 3-position with 3 -chloro, 2 or 3 bromo, or 1, 2, or 3 iodo; wherein $R_2$, $R_3$, $R_4$, $R_5$, $R_6$, $R_7$, and $R_8$ are hydrogen or alkyl of one to 4 carbon atoms, inclusive; wherein $C_mH_{2m}$ is alkylene of one to 9 carbon atoms, inclusive, with one to 4 carbon atoms, inclusive, between -$CHR_2$- and -O-; wherein $C_tH_{2t}$ represents (1) a valence bond or (2) alkylene of one to 10 carbon atoms, inclusive, substituted with zero, one, or 2 fluoro, with one to 7 carbon atoms, inclusive, between -$CR_3OH$- and the ring; wherein T is alkyl of one to 4 carbon atoms, inclusive, fluoro, chloro, trifluoromethyl, or —$OR_9$, wherein $R_9$ is hydrogen, alkyl of one to 4 carbon atoms, inclusive or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

2. A compound according to claim 1 wherein

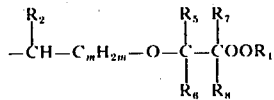

is —$(CH_2)_3$—O—$(CH_2)_2COOR_1$ wherein $R_1$ is as defined in claim 10.

3. A compound according to claim 2 wherein ~ OH is attached to the ring in alpha configuration.

4. A compound according to claim 3 wherein $C_tH_{2t}$ is straight chain alkylene of one to 4 carbon atoms with or without a fluoro or alkyl substituent on the carbon atom adjacent to the hydroxysubstituted carbon atom.

5. A compound according to claim 4 wherein the side chain hydroxy is in S configuration.

6. A compound according to claim 4 wherein $R_4$ is hydrogen.

7. A compound according to claim 6 wherein $R_3$ is hydrogen.

8. A compound according to claim 7 wherein $C_tH_{2t}$ is $(CH_2)_d$ wherein d is one, 2, 3, or 4.

9. A compound according to claim 8 wherein d is 2.

10. 4-Oxa-17-phenyl-18,19,20-trinor-PGF$_{1\alpha}$, a compound according to claim 9.

11. 4-Oxa-17-phenyl-18,19,20-trinor-PGF$_{1\alpha}$, ethyl ester, a compound according to claim 9.

12. A compound according to claim 6 wherein $R_3$ is methyl.

13. A compound according to claim 12 wherein $C_tH_{2t}$ is $(CH_2)_d$ wherein d is one, 2, 3, or 4.

14. A compound according to claim 13 wherein d is 2.

15. 4-Oxa-15-methyl-17-phenyl-18,19,20-trinor-PGF$_{1\alpha}$, a compound according to claim 14.

16. 4-Oxa-15-methyl-17-phenyl-18,19,20-trinor-PGF$_{1\alpha}$, ethyl ester, a compound according to claim 14.

17. A compound according to claim 4 wherein the side chain hydroxy is in R (epi) configuration.

18. A compound according to claim 17 wherein $R_4$ is hydrogen.

19. A compound according to claim 18 wherein $R_3$ is methyl.

20. A compound according to claim 19 wherein $C_tH_{2t}$ is $(CH_2)_d$ wherein d is one, 2, 3, or 4.

21. A compound according to claim 20 wherein d is 2.

22. 15-Epi-4-oxa-15-methyl-17-phenyl-18,19,20-trinor-PGF$_{1\alpha}$, a compound according to claim 21.

23. 15-Epi-4-oxa-15-methyl-17-phenyl-18,19,20-trinor-PGF$_{1\alpha}$, ethyl ester, a compound according to claim 21.

24. A compound according to claim 2 wherein ~ OH is attached to the ring in beta configuration.

25. A compound according to claim 24 wherein the side chain hydroxy is in S configuration.

26. A compound according to claim 24 wherein the side chain hydroxy is in R (epi) configuration.

27. A compound of the formula:

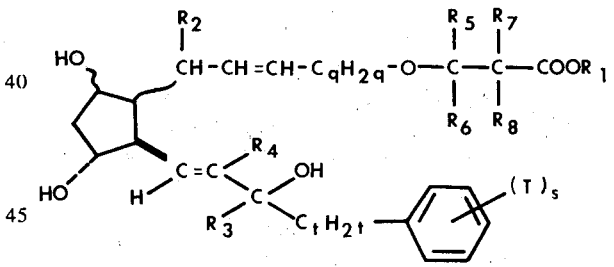

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive phenyl, phenyl substituted with one, 2, or 3chloro or alkyl of one to 4 carbon atoms, inclusive, or ethyl substituted in the β-position with 3-chloro, 2 or 3 bromo, or 1, 2, or 3 iodo; wherein $R_2$, $R_3$, $R_4$, $Rl_5$, $R_6$, $R_7$, and $R_8$ are hydrogen or alkyl of one to 4 carbon atoms, inclusive; wherein $C_qH_{2q}$ is alkylene of one to 7 carbon atoms, inclusive, with one or 2 carbon atoms between —CH=\ CH— and —O—; wherein $C_tH_{2t}$ represents a valence bond or alkylene of one to 10 carbon atoms, inclusivve, substituted with zero, one, or 2 fluoro, with one to 7 carbon atoms, inclusive, between —$CR_3OH$— and the ring; wherein T is alkyl of one to 4 carbon atoms, inclusive, fluoro, chloro, trifluoromethyl, or -$OR_9$, wherein $R_9$ is hydrogen, alkyl of one to 4 carbon atoms, inclusive, or tetrahydropyranyl, and s is zero, one, 2, or 3, with the proviso that no more than two I are other than alkyl; and wherein ~ indicates attachment of the group to the ring in alpha or beta configuration; including the lower alkanoates thereof, and the pharmacologically acceptable salts thereof when $R_1$ is hydrogen.

28. A compound according to claim 27 wherein

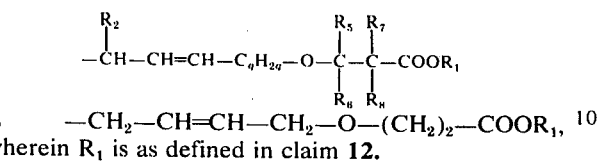

is  —$CH_2$—CH=CH—$CH_2$—O—$(CH_2)_2$—$COOR_1$, wherein $R_1$ is as defined in claim 12.

29. A compound of the formula:

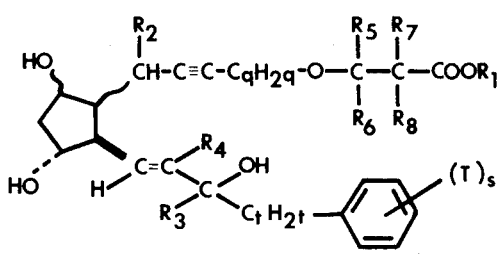

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl or one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, $RI_6$, $R_7$, and $R_8$ are hydrogen or alkyl of one to 4 carbon atoms, inclusive; wherein $C_qH_{2q}$ is alkylene of one to 7 carbon atoms, inclusive, with one or 2 carbon atoms between —C C— and —O—; wherein $C_tH_{2t}$ represents (1) a valence bond or (2) alkylene of one to 10 carbon atoms, inclusive, substituted with zero, one, or 2 fluoro, with one to 7 carbon atoms, inclusive, between —$CR_3OH$— and the ring; wherein T is alkyl of one to 4 carbon atoms, inclusive, fluoro, chloro, trifluoromethyl, or —$OR_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

30. A compound according to claim 29 wherein

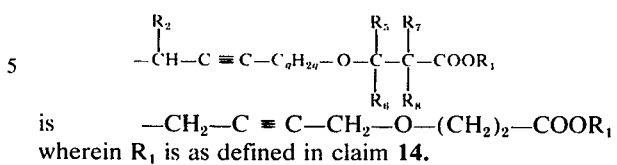

is  —$CH_2$—C≡C—$CH_2$—O—$(CH_2)_2$—$COOR_1$ wherein $R_1$ is as defined in claim 14.

31. A compound of the formula:

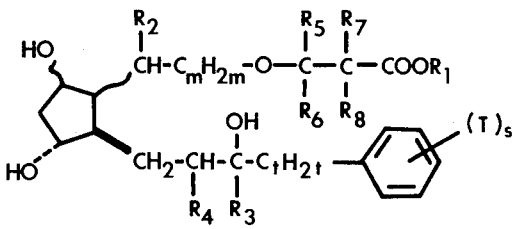

wherein $R_1$ is hydrogen, alkyl of one to 8 carbon atoms, inclusive, cycloalkyl of 3 to 10 carbon atoms, inclusive, aralkyl of b 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, $RI_6$, $R_7$, and $R_8$ are hydrogen or alkyl of one to 4 carbon atoms, inclusive; wherein $C_mH_{2m}$ is alkylene of one to 9 carbon atoms, inclusive, with one to 4 carbon atoms, inclusive, between —$CHR_2$— and —O—; wherein $C_tH_{2t}$ represents (1) a valence bond or (2) alkylene of one to 10 carbon atoms, inclusive, substitued with zero, one, or 2 fluoro, with one to 7 carbon atoms, inclusive, between —$CR_3OH$— and the ring; wherein T is alkyl of one to 4 carbon atoms, inclusive, fluoro, chloro, trifluoromethyl, or —$OR_9$, wherein $R_9$ is hydrogen, alkyl or one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

32. A compound according to claim 31 wherein

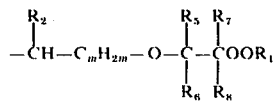

is  —$(CH_2)_3$—O—$(CH_2)_2$—$COOR_1$, wherein $R_1$ is as defined in claim 31.

* * * * *

UNITED STATES PATENT OFFICE
CERTIFICATE OF CORRECTION

Patent No. 3,983,157     Dated September 28, 1976

Inventor(s) Gordon L. Bundy

It is certified that error appears in the above-identified patent and that said Letters Patent are hereby corrected as shown below:

Column 2, line 11 "$-C_nH_2C_n-$" should read -- $-C_nH_2n-$ --.
Column 2, line 19 "$-CH\equiv CH-$" should read -- $-CH=CH-$ --.
Column 2, line 32 "$-OR_8,$" should read -- $-OR_9,$ --.
Column 2, line 32 "$R_8$" should read -- $R_9$ --.
Column 2, line 39 "XXI" should read -- XXII --.
Column 2, line 57 "EEIV," should read -- XXIV, --.
Column 3, line 24 "3-position" should read -- β-position --.
Column 3, line 47 
$$\begin{array}{c} R_7 \\ | \\ -COOR_1 \\ | \\ R_8 \end{array}$$
should read --
$$\begin{array}{c} R_7 \\ | \\ -C-COOR_1 \\ | \\ R_8 \end{array}$$
--.

Column 3, line 51 "claim 10." should read -- claim 1. --.
Column 3, line 61 "claim 4" should read -- claim 5 --.
Column 4, line 56 "$R1_5,$" should read -- $R_5,$ --.
Column 4, line 59 "$-CH=\lambda CH-$" should read -- $-CH=CH-$ --.
Column 4, line 68 "two I are" should read -- two T are --.
Column 5, line 11 "claim 12." should read -- claim 27. --.
Column 5, line 31 "or" third occurrence should read -- of --.
Column 5, line 34 "$R1_6,$" should read -- $R_6,$ --.
Column 5, lines 37-8 "$-C\ C-$" should read -- $-C\equiv C-$ --.
Column 6, line 8 "claim 14." should read -- claim 29. --.
Column 6, line 23 "of b 7" should read -- of 7 --.
Column 6, line 27 "$R1_6,$" should read -- $R_6,$ --.
Column 6, line 27 "Rare" should read -- $R_8$ are --.

UNITED STATES PATENT OFFICE
CERTIFICATE OF CORRECTION

Patent No. 3,983,157   Dated September 28, 1976

Inventor(s) Gordon L. Bundy

It is certified that error appears in the above-identified patent and that said Letters Patent are hereby corrected as shown below:

Column 6, line 37 "or" should read -- of --.
Column 6, line 47 "-C-COOR$_1$" should read -- -C——C-COOR$_1$ --.

Signed and Sealed this second Day of August 1977

[SEAL]

Attest:

RUTH C. MASON
*Attesting Officer*

C. MARSHALL DANN
*Commissioner of Patents and Trademarks*